US006037121A

United States Patent [19]
Garkavtsev et al.

[11] Patent Number: 6,037,121
[45] Date of Patent: *Mar. 14, 2000

[54] DNA SEQUENCE ENCODING A TUMOR SUPPRESSOR GENE

[75] Inventors: Igor Garkavtsev, Cambridge, Mass.; Karl Riabowol, Calgary, Canada; Andrei Gudkov, Glencoe, Ill.

[73] Assignees: University Technologies International Inc., Calgary, Canada; University of Illinois, Chicago, Ill.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/569,721

[22] Filed: Dec. 8, 1995

[51] Int. Cl.$^7$ .............................. C12Q 1/68; C07H 21/04
[52] U.S. Cl. .......................... 435/6; 435/7.21; 435/440; 435/455; 435/320.1; 435/325; 536/23.1
[58] Field of Search ........................... 435/6, 69.1, 172.1, 435/172.3, 320.1, 325, 243, 4, 455, 375, 377, 440, 7.21; 536/23.1, 24.31, 24.1, 24.5

[56] References Cited

U.S. PATENT DOCUMENTS

| | | | |
|---|---|---|---|
| 5,217,889 | 6/1993 | Roninson et al. | 435/6 |
| 5,811,234 | 9/1998 | Roninson et al. | 435/6 |

FOREIGN PATENT DOCUMENTS

| | | |
|---|---|---|
| WO 90/02569 | 3/1990 | WIPO . |
| WO 92/00329 | 1/1992 | WIPO . |
| WO 95/15334 | 6/1995 | WIPO . |
| WO 95/21253 | 8/1995 | WIPO . |
| WO 95/23855 | 9/1995 | WIPO . |
| WO 95/25429 | 9/1995 | WIPO . |

OTHER PUBLICATIONS

Berendsen H. "A Glimpse of the Holy Grail?" Science vol. 282:642–643, Oct. 1998.
Hiller et al, Database EST on MPSRCH accession No. T60958, Feb. 13, 1995.
Levine, A.J., "The Tumor Suppressor Genes", *Annu. Rev. Biochem.* 62:623–651 (1993).
Hunter, T. et al., "Cyclins and Cancer II: Cyclin D and CDK Inhibitors Come of Age", *Cell* 79:573–582 (1994).
Gudkov, A.V. et al., "Isolation of genetic suppressor elements, inducing resistance to topoisomerase II–interactive cytotoxic drugs, from human topoisomerase II cDNA", *Proc. Natl. Acad. Sc. USA* 90:3231–3235 (1993).
Straus, D. et al., "Genomic subtraction for cloning DNA corresponding to deletion mutations", *Proc. Natl. Acad. Sc. USA* 87:1889–1893 (1990).
Lisitsyn, N. et al., "Cloning the Differences Between Two Complex Genomes", *Science* 259:946–951 (1993).
Yaswen, P. et al., "Down–regulation of a calmodulin–related gene during transformation of human mammary epithelial cells", *Proc. Natl. Acad. Sc. USA* 87:7360–7364 (1990).

Miller, A.D. et al., "Improved Retroviral Vectors for Gene Transfer and Expression", *Biotechniques* 7:980–986 (1989).
Serrano, M. et al., "A new regulatory motif in cell–cycle control causing specific inhibition of cyclin D/CDK4", *Nature* 366:704–707 (1993).
Defeo–Jones, D., "Cloning of cDNAs for cellular proteins that bind to the retinoblastoma gene product", *Nature* 352:251–254 (1991).
Aharon, T. et al., "Selective Destabilization of Short–Lived mRNAs with the Granulocyte–Macrophage Colony–Stimulating Factor AU–Rich 3' Noncoding Region is Mediated by a Cotranslational Mechanism", *Mol. Cell. Biol.* 13:1971–1980 (1993).
Guan, K. et al., "Growth suppression by p18, a p16$^{INK4/MTS1}$ and p14$^{INK4B/MTS2}$–related CDK6 inhibitor, correlates with wild–type pRb function", *Genes & Dev.* 8:2939–2952 (1994).
Harper, J.W. et al., "The p21 Cdk–Interacting Protein Cip 1 is a Potent Inhibitor of G1 Cyclin–Dependent Kinases", *Cell* 75:805–816 (1993).
El–Deiry, W.S. et al., "WAF1, a Potential Mediator of p53 Tumor Suppression", *Cell* 75:817–825 (1993).
Kamb, A. et al., "A Cell Cycle Regulator Potentially Involved in Genesis of Many Tumor Types", *Science* 264:436–440 (1994).
Nobori, T. et al., "Deletions of the cyclin–dependent kinase–4 inhibitor gene in multiple human cancers", *Nature* 368:753–756 (1994).
Riabowol, K. et al., "The cdc2 Kinase Is a Nuclear Protein That Is Essential for Mitosis in Mammalian Cells", *Cell* 57:393–401 (1989).
Yang, Y. et al., "An approach for treating the hepatobiliary disease of cystic fibrosis by somatic gene transfer" *Proc. Nat'l. Acad. Sci. USA* 90: 4601–4605 (1993).
Atadja, P. et al., "Increased activity of p53 in senescing fibroblasts" *Proc. Nat'l. Acad. Sci. USA* 92: 8348–8352 (1995).
Grudkov, A. et al., "Cloning mammalian genes by expression selection of genetic suppressor elements: Associate of kinesin with drug resistance and cell immortalization" *Proc. Nat'l Acad. Sci. USA* 91: 3744–3798 (1994).
Garkavtsev et al. (1996), "Suppression of the novel growth inhibitor p33$^{ing\ 1}$ promotes neoplastic transformation", *Nature Genetics*, 14(4):415–420.
Weinberg, Robert A. (1991), "Tumor Suppressor Genes", *Science*, 254:1138–1146.
Hillier et al. (Feb. 1995), "Database EMBL Entry HS12525", *WashU–EST Project*.

*Primary Examiner*—John S. Brusca
*Assistant Examiner*—Sean McGarry
*Attorney, Agent, or Firm*—Burns, Doane, Swecker & Mathis, LLP

[57] ABSTRACT

The invention provides novel tumor suppressor genes, methods for making and using these and related tumor suppressor genes and proteins and peptides, and nucleic acids encoding these and related tumor suppressor proteins and peptides.

6 Claims, 5 Drawing Sheets

```
   1  CTG ACC CGA GGG TGG GGC CGC GCG TGG CCG TGG AAA CAG ATC CTG AAG GAG CTA GAC GAG

61  TGC TAC GAG CGC TTC AGT CGC GAG ACA GAC GGG GCG CAG AAG CGG CGG ATG CTG CAC TGT
   1                                                                  met leu his cys 121  GTG CAG CGC GCG CTG ATC CGC AGC CAG GAG CTG GGC GAC GAG AAG ATC CAG ATC GTG AGC
   5  val gln arg ala leu ile arg ser gln glu leu gly asp glu lys ile gln ile val ser 181  CAG ATG GTG GAG CTG GTG GAG AAC CGC ACG CGG CAG GTG GAC AGC CAC GTG GAG CTG TTC
  25  gln met val glu leu val glu asn arg thr arg gln val asp ser his val glu leu phe 241  GAG GCG CAG CAG GAG CTG GGC GAC ACA GTG GGC AAC AGC GGC AAG GTT GGC GCG GAC AGG
  45  glu ala gln gln glu leu gly asp thr val gly asn ser gly lys val gly ala asp arg 301  CCC AAT GGC GAT GCG GTA GCG CAG TCT GAC AAG CCC AAC AGC AAG CGC TCA CGG CGG CAG
  65  pro asn gly asp ala val ala gln ser asp lys pro asn ser lys arg ser arg arg gln 361  CGC AAC AAC GAG AAC CGT GAG AAC GCG TCC AGC AAC CAC GAC CAC GAC GAC GGC GCC TCG
  85  arg asn asn glu asn arg glu asn ala ser ser asn his asp his asp asp gly ala ser 421  GGC ACA CCC AAG GAG AAG AAG GCC AAG ACC TCC AAG AAG AAG AAG CGC TCC AAG GCC AAG
 105  gly thr pro lys glu lys lys ala lys thr ser lys lys lys lys arg ser lys ala lys 481  GCG GAG CGA GAG GCG TCC CCT GCC GAC CTC CCC ATC GAC CCC AAC GAA CCC ACG TAC TGT
 125  ala glu arg glu ala ser pro ala asp leu pro ile asp pro asn glu pro thr tyr cys 541  CTG TGC AAC CAG GTC TCC TAT GGG GAG ATG ATC GGC TGC GAC AAC GAC GAG TGC CCC ATC
 145  leu cys asn gln val ser tyr gly glu met ile gly cys asp asn asp glu cys pro ile 601  GAG TGG TTC CAC TTC TCG TGC GTG GGG CTC AAT CAT AAA CCC AAG GGC AAG TGG TAC TGT
 165  glu trp phe his phe ser cys val gly leu asn his lys pro lys gly lys trp tyr cys 661  CCC AAG TGC CGG GGG GAG AAC GAG AAG ACC ATG GAC AAA GCC CTG GAG AAA TCC AAA AAA
 185  pro lys cys arg gly glu asn glu lys thr met asp lys ala leu glu lys ser lys lys 721  GAG AGG GCT TAC AAC AGG TAG TTT GTG GAC AGG CGC CTG GTG TGA GGA GGA CAA AAT AAA
 205  glu arg ala tyr asn arg ***

781  CCG TGT ATT TAT TAC ATT GCT GCC TTT GTT GAG GTG CAA GGA GTG TAA AAT GTA TAT TTT
 841  TAA AGA ATG TTA GAA AAG GAA CCA TTC CTT TCA TAG GGA TGG CAG TGA TTC TGT TTG CCT
 901  TTT GTT TTC ATT GGT ACA CGT GTA ACA AGA AAG TGG TCT GTG GAT CAG CAT TTT AGA AAC
 961  TAC AAA TAT AGG TTT GAT TCA ACA CTT AAG TCT CAG ACT GAT TTC TTG CGG GAG GAG GGG
1021  GAC TAA ACT CAC CCT AAC ACA TTA AAT GTG GAA GGA AAA TAT TTC ATT AGC TTT TTT ATT
1081  TTA ATA CAA GTA ATA TTA TTA CTT TAT GAA CAA TTT TTT TTA ATT GGC CAT GTC GCC AAA
1141  AAT ACA GCC TAT AGT AAA TGT GTT TCT TGC TGC CAT GAT GTA TAT CCA TAT AAC AAT TCA
1201  GTA ACA AAG GTT TAA AGT TTG AAG ATT ATT TTT AAA AAG GGT AAA AGG TTA AAT TTT ACA
1261  TGA CAG ATA TTT TAT CTA TTG GCC TGT TCC CCA AAT GGC CAT TTT AAA ATG CTT GGG TAC
1321  ACT TCT CTT AAG TGG TCT AGT CAA GGA ACC TCA AGT CAT GCT TTT GCT ATC ACC AAT CAT
1381  AGT GTA CCC ATC TTT AAT TTA TAT CAG GTG TAT AAA TGT ACA TTT CCA AAT GAA CTT GCA
1441  CTG TAA TAT TAT AAT TGG AAG TGC AGT CAG CAG TAG CTG TCG GAG CTA ATG TCA AAT TA
1501  TGT GCA AAG GTC TGC TTC CTG CTG TAT GTG AGC TGT AAA AAT GTT ACG TGA AGA AAT AAA
1561  TGA AAC TTG GCC AGT TTG TTC CTC TAG TAG TAT ATT TAA TTT TGA CAT AAG TAA CTT TTA
1621  AAA TTT GTC TTA AAA ATT TAT ACA CCA GCA ATT TAG ACA AAG CCT TAA GCA AAT TTT GTA
1681  TTA TTG TTC TCA CTT ATT ATT AAT AAT GAA GTA GAA GTT ACT TAA TTG CCA GCA AAT AAA
1741  TAC GTG TCA AAA AAG AAT CTG TAT TCA GAC CCC TGG GGT CAG GAA ATT ACT GCC CCA CTT
1801  GTC AAG TTC AGC CCA CCA TCT GTT TGA ACA TTA TAT GAA GTT TAA ATT CTA GTG TCC ATA
1861  AAT AAA GTT TCA GCG GCA CCC CAA AAA AAA AAA AAA AAA
```

FIG. 2

Overexpression of p33^ING1 blocks cell growth

Hs578T breast cancer cells · · · Hs68 primary human diploid fibroblasts

Expression of *ING1*/p33$^{ING1}$ in low & high passage primary HDFs mRNA levels by RT-PCR Protein levels by western blot

DNA SEQUENCE ENCODING A TUMOR SUPPRESSOR GENE

FIELD OF THE INVENTION

This invention relates to novel tumor suppressor genes, to methods for making and using these and related tumor suppressor genes and proteins and peptides, and to nucleic acids encoding these and related tumor suppressor proteins and peptides.

REFERENCES

The following references are cited in the application as numbers in brackets ([]) at the relevant portion of the application.

1. Levine, A. J., "The Tumor Supressor Genes", *Annu. Rev. Biochem.* 62:623–651 (1993).
2. Hunter, T. et al., "Cyclins and Cancer II: Cyclin D and CDK Inhibitors Come of Age", *J. Cell* 79:573–582 (1994).
3. Gudkov, A. V. et al., "Isolation of genetic suppressor elements, inducing resistance to topoisomerase II-interactive cytotoxic drugs, from human topoisomerase II cDNA", *Natl. Acad. Sc. USA* 90:3231–3235 (1993).
4. Straus, D. et al., "Genomic subtraction for cloning DNA corresponding to deletion mutations", *Proc. Natl. Acad. Sc. USA* 87:1889–1893 (1990).
5. Lisitsyn, N. et al., "Cloning the Differences Between Two Complex Genomes", *Science* 259:946–951 (1993).
6. Yaswen, P. et al., "Down-regulation of a calmodulin-related gene during transformation of human mammary epithelial cells", *Proc. Natl. Acad. Sc. USA* 87:7360–7364 (1990).
7. Miller, A. D. et al., "Improved Retroviral Vectors for Gene Transfer and Expression", *Biotechniques* 7:980–986 (189).
8. Serrano, M. et al., "A new regulatory motif in cell-cycle control causing specific inhibition of cyclin D/CDK4", *Nature* 366:704–707 (1993).
9. Defeo-Jones, D., "Cloning of cDNAs for cellular proteins that bind to the retinoblastoma gene product", *Nature* 352:251–254 (1991).
10. Aharon, T. et al., "Selective Destabilization of Short-Lived mRNAs with the Granulocyte-Macrophage Colony-Stimulating Factor AU-Rich 3' Noncoding Region is Mediated by a Cotranslational Mechanism", *Mol. Cell. Biol.* 13:1971–1980 (1993).
11. Guan, K. et al., "Growth suppression by p18, a p16$^{INK4/MTS1}$ and p14$^{INK4B/MTS2}$- related CDK6 inhibitor, correlates with wild-type pRb function", *Genes & Dev.* 8:2939–2952 (1994).
12. Harper, J. W. et al., "The p21 Cdk-Interacting Protein Cip1 is a Potent Inhibitor of G1 Cyclin-Dependent Kinases", *Cell* 75:805–816 (1993).
13. El-Deiry, W. S. et al., "WAF1, a Potential Mediator of p53 Tumor Suppression", *Cell* 75:817–825 (1993).
14. Kamb, A. et al., "A Cell Cycle Regulator Potentially Involved in Genesis of Many Tumor Types", *Science* 264:436–440 (1994).
15. Nobori, T. et al., "Deletions of the cyclin-dependent kinase-4 inhibitor gene in multiple human cancers", *Nature* 368:753–756 (1994).
16. Riabowol, K. et al., "The cdc2 Kinase Is a Nuclear Protein That Is Essential for Mitosis in Mammalian Cells", *Cell* 57:393–401 (1989).
17. Sambrook, J. et al., "Molecular Cloning" (2nd.Ed.), *A Laboratory Manual, Cold Spring Harbor Laboratory Press* (1989).
18. Harlow, E. et al., "Antibodies", *A Laboratory Manual, Cold Spring Harbor Laboratory* (1988).
19. Yang, Y. et al., "An approach for treating the hepatobiliary disease of cystic fibrosis by somatic gene transfer" *Proc. Nat'l. Acad. Sci. USA* 90, 4601–4605 (1993).
20. Atadja, P. et al., "Increased activity of p53 in senescing fibroblasts" *Proc. Nat'l. Acad. Sci. USA* 92, 8348–8352 (1995).

The disclosure of the above publications, patents and patent applications are herein incorporated by reference in their entirety to the same extent as if the language of each individual publication, patent and patent application were specifically and individually included herein.

BACKGROUND OF THE INVENTION

Many cancers originate and progress by accumulating mutations in one or more genes. Such mutations which result in cancer formation can be in proto-oncogenes or in tumor supressor genes. Mutations in tumor supressor genes result in loss of function, and therefore act in a recessive fashion to wild-type genes. Oncogenes, in contrast, act in dominant fashion to wild-type alleles and, therefore, are not usually inherited through the germ lines. The tumor supressor genes, however, are found in inherited predispositions to cancer and are inherited as a dominant predisposition because of the high frequency of a second genetic event such as reduction in homozygosity[1].

Several tumor supressor genes have been identified. Examples include the Rb gene, which is involved in retinoblastoma and osteosarcoma; p53, which is involved in osteosarcoma and adrenocortical, breast and brain cancers; WT-1, which is involved in Wilms' tumor, nephroblastoma and neurofibromatosis; adenomatous polyposis coli (APC), which is involved in adenomatous polyposis; and deleted colorectal cancer (DCC), which is involved with a somatic mutation in the colon.

The negative regulation of cell growth is affected by tumor supressor proteins that regulate the cell cycle by different mechanisms[2]. The gene cloned and sequenced as described herein, p33$^{IG1}$, represents a new tumor suppressor gene which is expressed in normal mammary epithelial cells, but expressed only at lower levels in several cancerous mammary epithelial cell lines.

Known applications of sequenced genes include use of the DNA sequence (or analogs thereof) or of RNA or amino acid sequences derived from these DNA sequences for diagnosis or treatment of the corresponding disease. Accordingly, p33$^{IG1}$ is useful for the diagnosis and treatment of breast cancer.

SUMMARY OF THE INVENTION

The present invention is directed to a novel DNA sequence complementary to an mRNA coded for by an isolated gene (designated p33$^{IG1}$) found in normal breast tissue but found only at lower levels in cancerous breast tissue. The DNA sequence and/or the protein it encodes, and fragments or analogs thereof, are useful for diagnosing and treating breast cancer.

One aspect of the invention provides DNA isolates which are substantially identical to the DNA sequence of FIG. 2. Recombinant expression vectors comprising such DNA isolates and cells transformed with such recombinant expression vectors are also provided.

Another aspect of the invention provides DNA sequences greater than about 10 base pair (bp) in length which are capable of hybridizing under stringent conditions to the complement of the DNA sequence shown in FIG. 2. Recombinant expression vectors comprising such DNA sequences and cells transformed with such recombinant expression vectors are also provided.

One other aspect of the invention provides proteins encoded by DNA isolates substantially identical to the DNA sequence of FIG. 2.

Still another aspect of the invention provides peptides or proteins encoded by DNA sequences greater than about 10 base pair (bp) in length which are capable of hybridizing under stringent conditions to the complement of the DNA sequence shown in FIG. 2.

A further aspect of the invention provides methods for treating breast cancer comprising administering, via traditional pharmaceutical methods or gene therapy, an effective amount of the above-described DNA isolates, DNA sequences, proteins or peptides.

Another further aspect of the invention provides methods of decreasing cell proliferation of mammalian cells by selecting said cells and increasing expression of $p33^{IG1}$ in the cells. Likewise, methods of increasing cell proliferation by decreasing $p33^{IG1}$ expression in the cells are provided.

A yet further aspect of the invention provides a method for diagnosing breast cancer comprising: obtaining a biological sample comprising mammary cells suspected of being neoplastic and detecting whether or not the biological sample contains $p33^{IG1}$ or the DNA which encodes $p33^{IG1}$, wherein the presence of $p33^{IG1}$ or its DNA denotes non-cancerous cells.

A still further aspect of the invention provides a method for diagnosing breast cancer comprising: obtaining a biological sample comprising mammary cells suspected of being neoplastic; contacting said biological sample with at least one antibody to $p33^{IG1}$ under conditions wherein antibody binding to $p33^{IG1}$ occurs; and detecting whether or not said antibody binds to said cells, wherein binding to said cells indicates that said cells are non-cancerous.

DETAILED DESCRIPTION OF THE INVENTION

Figure 1A:
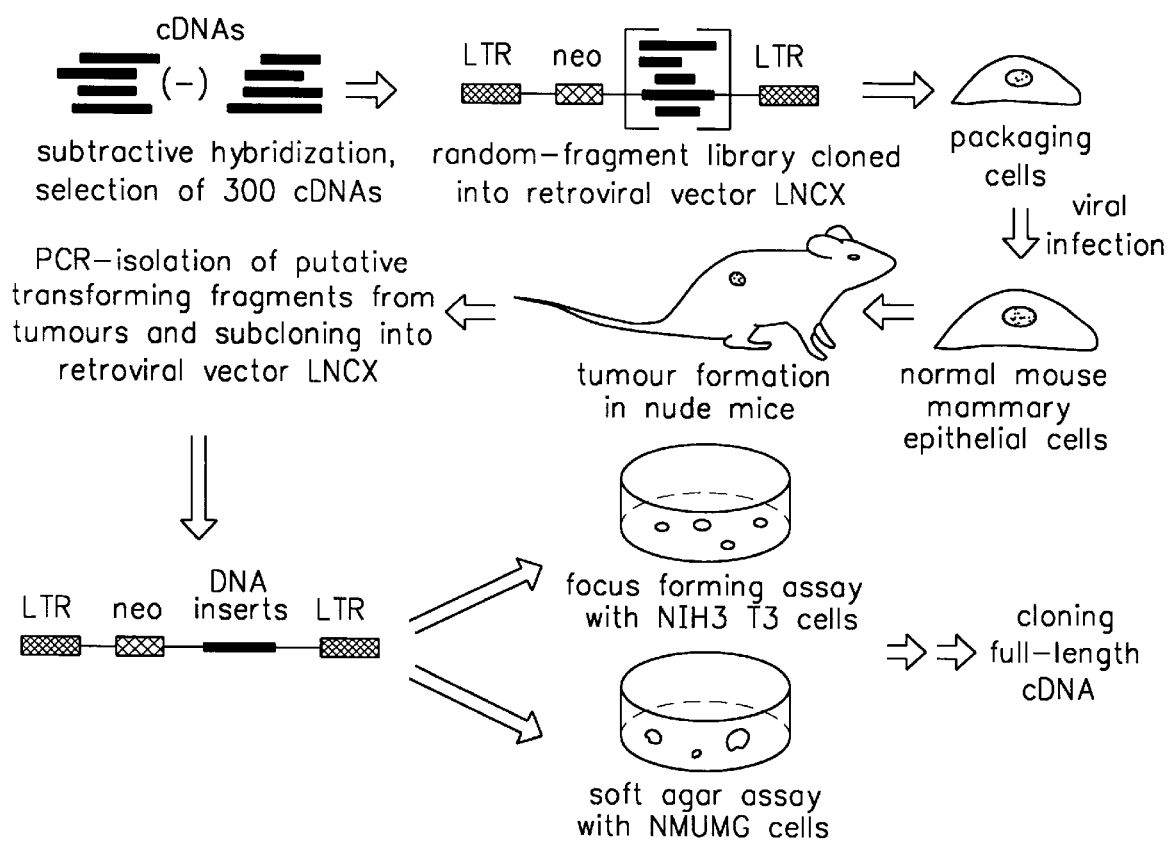
FIGS. 1A to 1C illustrate the strategy and biological assays used for cloning $p33^{IG1}$ FIG. 2 sets forth the cDNA sequence (SEQ ID NO. 1) and the predicted amino acid sequence (SEQ ID NO. 2) of $p33^{IG1}$.

The invention described herein relates to the discovery of a novel tumor suppressor gene, designated $p33^{IG1}$, found in normal mammary epithelial cells but found only at lower levels in several breast cancer cell lines.

Using a strategy based upon subtractive hybridization of normal and cancerous mammary epithelial cell mRNAs and the selection of genetic suppressor elements [3], we isolated a novel gene encoding a 33 kDa protein that is a potent inhibitor of cell growth. Acute expression of transfected constructs encoding this gene inhibited cell growth as estimated by decreased S-phase fraction and blocked entry into S-phase following needle microinjection. Chronic expression of antisense constructs resulted in tumor induction in vivo and in focus formation in vitro, and also conferred the ability to grow in soft agar.

Sequence analysis showed that a region of this protein is highly related to a variant of the $p16^{MTS1}$ tumor suppressor.

A. Definitions

As used herein the following terms have the following meanings:

"Antibody" means a molecule that binds to a known antigen.

"Antisense" and "Antisense nucleotides" means DNA or RNA constructs which block the expression of the naturally-occurring gene product. For example, in the present invention, use of a DNA construct that produces $p33^{IG1}$ antisense RNA blocks the expression of $p33^{IG1}$ by destroying or inactivating $p33^{IG1}$ mRNA.

"Biological sample" means a sample of mammalian cells. These cells may be part of a tissue or organ sample obtained, for example, by biopsy, or they may be individual cells, for example, blood cells or cells grown in tissue culture.

"Breast cancer" means any of various malignant neoplasms of the breast or mammary tissue.

"Cancerous Cell" means a cell in or from a neoplasm.

"Cell cycle" means the cyclic biochemical and structural events occurring during growth of cells. The cycle is divided into periods called : $G_o$, $Gap_1$ ($G_1$), DNA synthesis (S), $GAP_2$ ($G_2$), and mitosis (M)

"Cell division" means mitosis, i.e., the usual process of cell reproduction.

"Cell-proliferation-inhibiting-peptide compound" means a peptide or peptide-containing compound which inhibits cell proliferation, either in vitro or in vivo.

"Code" or "encode", when used with reference to a nucleotide's relation to a protein, mean the system whereby particular combinations of adjacent nucleotides control the insertion of particular amino acids in equivalent places in a protein molecule.

"Expression" means the production of a protein or nucleotide in the cell.

"Growth" means progression through the cell cycle with the result that two daughter cells are formed from each mother cell. "Actively growing" means that state wherein cells exhibit growth and cell division.

"Hyperplasticity" means an increase in cell number, excluding tumor formation.

"Label" means to incorporate into a compound a substance that is readily detected. Such substances include radioactive substances and fluorescent dyes, for example.

"Mammalian cell" means a cell in or from a mammal, either in a tissue or organ or in tissue culture.

"Neoplasia" means the process resulting in the formation and growth of an abnormal tissue that grows by cellular proliferation more rapidly than normal, and continues to grow after the stimuli that initiated the new growth cease.

"Neoplastic" describes the abnormal tissue that grows by cellular proliferation more rapidly than normal, and continues to grow after the stimuli that initiated the new growth cease.

"Normal cell" means a non-cancerous cell.

"Proliferation" means growth and reproduction, i.e., division of cells.

B. Synthesis and Methodoloqy

To identify gene products whose inactivation might contribute to the emergence and growth of cancer cells, a novel positive selection procedure that combines subtractive hybridization with an in vivo selection assay was used to identify putative growth-suppressor elements. An overview of the strategy used is shown in FIG. 1a.

Following a modified subtractive hybridization protocol [4,5], total cDNA from a normal mammary epithelial cell line [6] was hybridized independently with cDNAs from the breast cancer cell lines MCF-7, BT-483, BT-474, Hs-578T, ZR-75, MD-MB-468, MD-MB-435 and BT-20 which were obtained from the American Type Culture Collection. Subtracted cDNA, theoretically containing sequences more highly expressed in the phenotypically normal epithelial cells, was then used as a probe to screen a normal human fibroblast cDNA library.

Following screening, 300 cDNA clones were isolated, and their inserts were digested into fragments of 200–800 bps. The fragments were then recloned into the retroviral plasmid vector pLNCX [7]. After passage through the packaging line BOSC 23 [3], retroviruses containing the isolated fragments were used to infect normal mouse mammary epithelial cells (NMuMG). The infected cells were subsequently injected into nude mice.

Within 45 days, several mice developed tumors from which the cloned inserts were recovered by amplification using primers specific for pLNCX in polymerase chain reactions (PCR). Two different sequences were isolated from tumors, one of which was subsequently shown to be expressed in the antisense orientation. The primers used in the PCR amplification were:

5'-CCCCAAGCTTGTTAACTTCGATGGA-3' (SEQ ID NO. 7) (sense); and

5'-ATGGCGTTACTTAAGCTAGCTTGC-3' (SEQ ID NO. 8) (antisense).

Figure 1B:
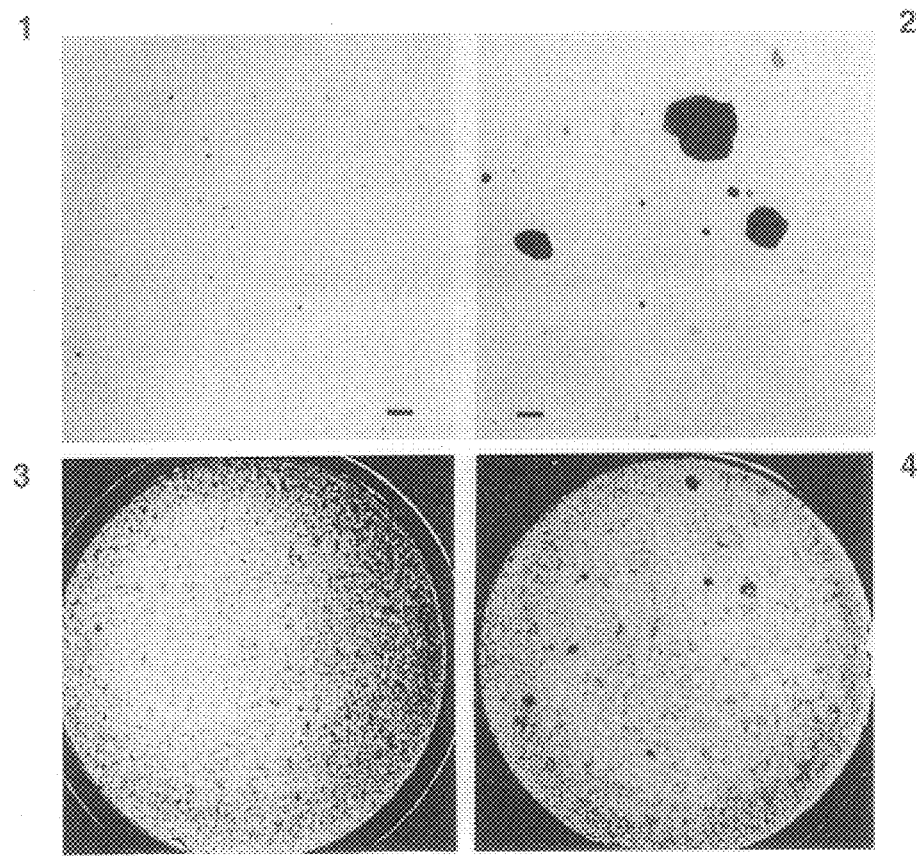

The antisense sequence isolated using the sense and antisense primers consistently showed the biological effects of increased cell proliferation in soft agar and in focus forming assays (FIG. 1b and Table 1). This 182 bp fragment represented nucleotides 781 to 963 of the complete cDNA shown in FIG. 2 that encodes a 33 kDa protein called p33$^{IG1}$ for Inhibitor of Growth.

After plating NMUMG cells infected with either control virus or with virus containing an insert of the antisense orientation of p33$^{IG1}$ in soft agar, cells receiving the insert formed, on average, at least 50 times the number of colonies as cells infected with virus alone. Similar results were obtained following transfection of the retroviral construct into NIH3T3 cells, where PLNCX containing the insert of the antisense orientation of p33$^{IG1}$ resulted in the formation of 2.3 times the number of generally larger foci than vector alone.

These results corroborated the observations we had made in the nude mouse assay that the p33$^{IG1}$ sequence corresponds to a gene whose product plays a significant role in regulating cell growth.

In order to isolate the gene corresponding to the fragment showing biological effects, normal human fibroblast and HeLa cell libraries were screened with the fragment, resulting in the isolation of 11 positive clones. Two clones contained full-length cDNAs whose sequence, shown in FIG. 2, revealed that p33$^{IG1}$ was homologous to a variant of the 16 kDa MTS1 tumor suppressor [8] in a domain encompassing amino acids 9 through 60 of p33$^{IG1}$The protein also shows more limited homology to a protein that binds the retinoblastoma tumor suppressor (Rb-BP2) [9] within its carboxyl region, suggesting that it might serve as a direct link between two major classes of tumor suppressors.

Figure 1C:
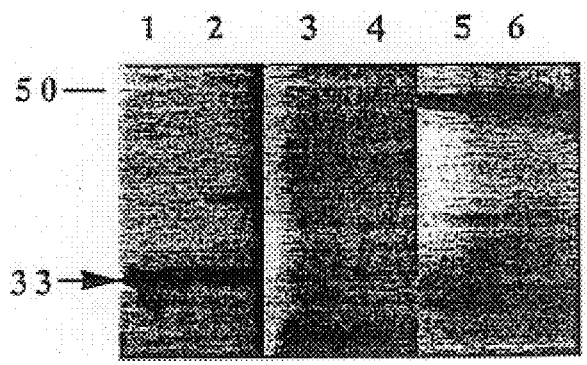

Use of a polyclonal antibody raised against a glutathione-S-transferase (GST) fusion with p33$^{IG1}$ revealed a protein of 33 kDa by Western blot analysis of human and mouse cell extracts (FIG. 1c).

To determine whether the level of p33$^{IG1}$ was decreased in cells infected with viral constructs containing the antisense orientation, we prepared lysates from control NMuMG cells and from NMuMG cells infected with antisense p33$^{IG1}$ that had grown and formed colonies in semi-solid medium. Results of Western blot analysis showed that chronic expression of antisense construct reduced the expression of the endogenous p33$^{IG1}$ gene by approximately 90% in cells that had acquired the ability to grow in soft agar (FIG. 1c, lane 6) compared to control parental cells (FIG. 1c, lane 5).

We also noted that the p33$^{IG1}$ cDNA contains several AU-rich elements (AREs) in the 3' untranslated region of the clone (FIG. 2) which are believed to be involved in the destabilization of specific mRNAs [10].

Since p33$^{IG1}$ was originally isolated by subtractive hybridization between normal and transformed epithelial cDNAs, we next examined the levels of p33$^{IG1}$ mRNA expression in different normal and breast cancer cell lines. Our preliminary results from Northern blot analysis show that p33$^{IG1}$ is expressed at considerably lower levels (approximately 2–8 fold as estimated by scanning densitometry) in BT-20, ZR-75, MDA-MB-435 and T-47D breast cancer cells compared to MDA-MB-468 and SK-BR-3 breast cancer cells and to normal Hs68 fibroblasts.

Figure 3A:
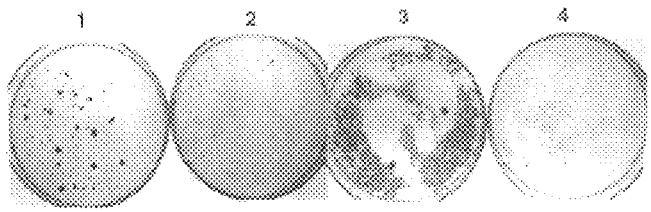
FIGS. 3A to 3C illustrate the effects of $p33^{IG1}$ overexpression.

Isolation of a DNA fragment that was capable of inducing tumors, foci and growth in soft agar when expressed in the antisense orientation, suggested that the cellular role of p33$^{IG1}$ is to negatively regulate growth. To test this idea, full-length p33$^{IG1}$ was cloned into the mammalian expression vector pBK in the sense orientation (p33$^{IG1}$-S). This construct and the plasmid vector, both of which contain neomycin resistance genes and a cytomegalovirus (CMV) promoter, were transfected into human breast cancer (Hs578T) and normal fibroblast (Hs68) cells. Following growth of the cells in antibiotic for 3 weeks, a large number of stable transformants were recovered from cells transfected with vector, whereas very few colonies were visible in plates of cells transfected with the sense orientation of p33$^{IG1}$ (FIG. 3a).

To corroborate the results of these chronic assays, we examined the effect of microinjecting these constructs, together with non-specific antibodies, on the ability of normal diploid fibroblasts to initiate DNA synthesis. Arrows in panels 1 and 3 of FIG. 3b identify cells injected with sense (S) and antisense ($\alpha$S) constructs, respectively, which were visualized by staining for the presence of coinjected non-specific antibodies using indirect immunofluorescence.

Figure 3B:
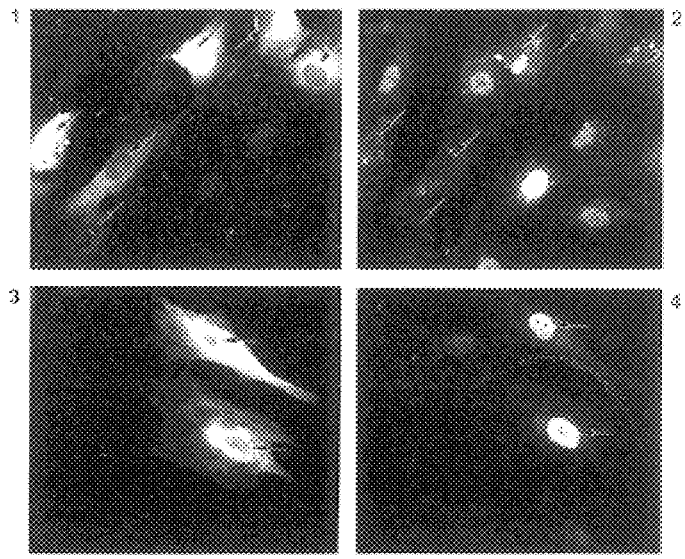

Arrows in panels 2 and 4 of FIG. 3b show that cells injected with p33$^{IG1}$-S failed to incorporate bromodeoxyuridine (BrdU) (panel 2) over a 36 hour time course after injection. In contrast, those injected with p33$^{IG1}$-$\alpha$S entered S phase (panel 4) as estimated by staining with $\alpha$-BrdU antibodies.

Figure 3C:
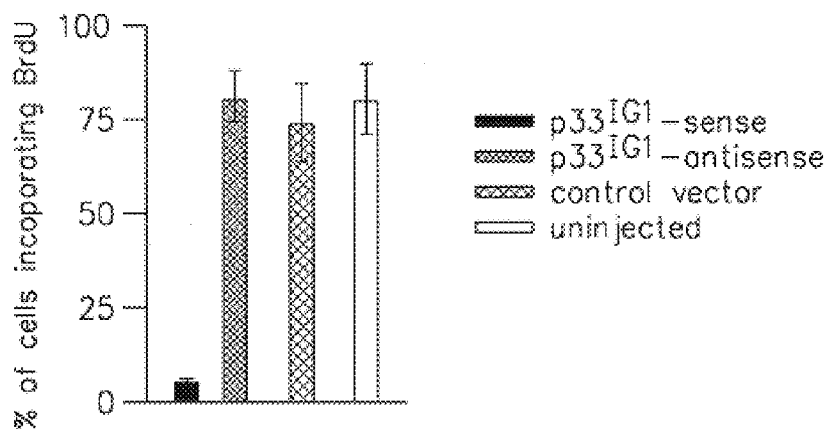

FIG. 3c shows the combined results of 5 separate experiments, which indicated that injection of the pBK vector or of p33$^{IG1}$-$\alpha$S constructs had no appreciable effect upon the ability of injected cells to incorporate BrdU, whereas injection of p33$^{IG1}$-S blocked the ability of cells to enter into and proceed through S phase. Similar results were obtained in larger populations of cells that were electroporated with vector, sense and antisense construct DNAs together with a construct encoding the CD20 surface marker.

Such co-transfections allowed the analysis of DNA content in cells that had taken up DNA by staining for CD20 and subsequent analysis by fluorescence activated cell sorting (FACS). As shown in Table 2, the CD20-expressing population co-transfected with p33$^{GS1}$-S had, on average, 63.1% of cells in G0/G1 whereas those cotransfected with vector had 33.6% of cells in G0/G1 when cells were fixed and stained 48 hours after electroporation.

These results, using several independent methods, indicate that the overexpression of p33$^{IG1}$ inhibits cell growth in both transient and chronic assays, most likely by arresting cells in the G1 phase of the cell cycle.

Figure 4A:
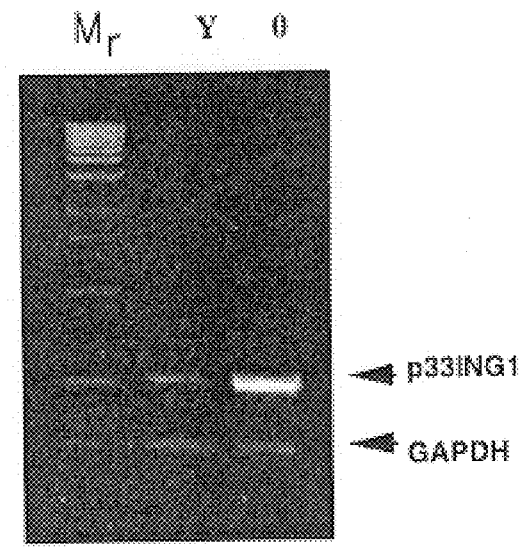
FIGS. 4A and 4B illustrate the expression of $p33^{IG1}$ in proliferation competent and in senescent human fibroblasts.
Figure 4B:
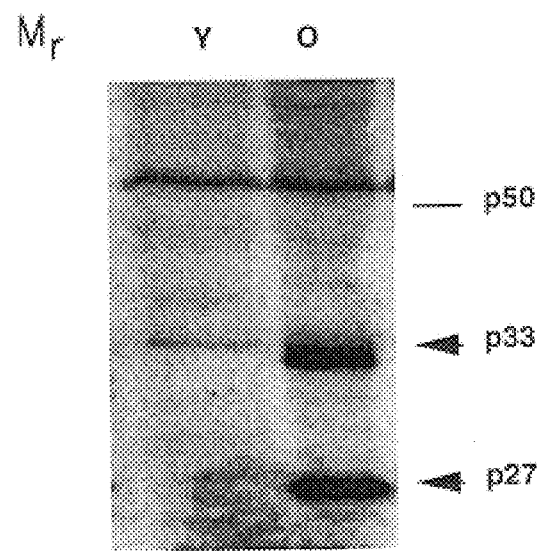

Since the activity of the tumor suppressor genes increases in senescent cells [20], we next checked p33$^{IG1}$ activity in low and high passage cells. As shown in FIGS. 4a and 4b, p33$^{IG1}$ expression (and the level of the p33$^{IG1}$ protein) increased several-fold when cells approached the end of their in vitro replicative lifespan.

These data demonstrate that p33$^{IG1}$ is a novel inhibitor of cell growth and a candidate tumor suppressor. Additional experiments also indicate that p33$^{IG1}$ is localized in the nucleus of cells, which is consistent with p33$^{IG1}$ functioning as a tumor suppressor. Since p33$^{IG1}$ shows sequence similarities to p16$^{MTS1}$ and to Rb-BP2, we are now examining whether the p33$^{IG1}$ protein interacts with other known regulators of the cell cycle, particularly those that are preferentially active during the early phases of G1, and whether it binds to DNA in a sequence-specific manner.

Such studies, as well as more comprehensive analyses of the expression of p33$^{IG1}$ in normal and transformed cell lines and tissues, will allow us to determine if it functions in regulating transcription as do the tumor suppressors p53 and p105$^{Rb}$. Alternatively, p33$^{IG1}$ might play a role in the regulation of cyclin-dependent kinases (CDKs), as reported recently for the family of CDK inhibitors including p18[11], p21[12,13] and the candidate tumor suppressor p16$^{MTS1}$[8] to which a portion of the p33$^{IG1}$ sequence shows a high degree of homology, and which has been reported to be the MTS1 multiple tumor suppressor locus of human chromosome 9p21 that is inactivated in many type of human tumors [14,15].

It is expected that several p33$^{IG1}$ related peptides will be useful in the present invention. In particular, p33$^{IG1}$, its analogs and related proteins and peptides which are effective in suppressing the proliferation of cancerous cells are preferred.

Included within the scope of the p33$^{IG1}$ as that term is used herein are p33$^{IG1}$'s having the amino acid sequence set forth in FIG. 2, glycosylated or deglycosylated derivatives of p33$^{IG1}$, homologous amino acid sequence variants of the sequence of FIG. 2, and homologous in vitro-generated variants and derivatives of p33$^{IG1}$, which are capable of exhibiting a biological activity in common with the p33$^{IG1}$ of FIG. 2. p33$^{IG1}$ biological activity is defined as either: (1) immunological cross-reactivity with at least one epitope of native p33$^{IG1}$, or (2) the possession of at least one cell proliferation, cell regulatory or tumor suppressive function qualitatively in common with native p33$^{IG1}$s. One example of the qualitative biological activity of p33$^{IG1}$ is its ability to inhibit cell growth as estimated by decreasing the S-phase fraction in a population of cells.

Immunologically cross-reactive, as used herein, means that the candidate polypeptide is capable of competitively inhibiting the qualitative biological activity of the native p33$^{IG1}$, having this activity with polyclonal antisera raised against the known active analog. Such antisera are prepared in conventional fashion by injecting goats or rabbit, for example, subcutaneously with the known active analog in complete Freund's adjuvant, followed by booster intraperitoneal or subcutaneous injection in incomplete Freunds.

This invention is particularly concerned with amino acid sequence variants of native p$^{IG1}$. Amino acid sequence variants of the p33$^{IG1}$ are prepared with various objectives in mind, including increasing the affinity of the p33$^{IG1}$ for its binding partner, facilitating the stability, purification and preparation of the p33$^{IG1}$, modifying its biological half-life, improving therapeutic efficacy, and lessening the severity or occurrence of side effects during therapeutic use of the p33$^{IG1}$.

Amino acid sequence variants of the p33$^{IG1}$ fall into one or more of three classes: insertional, substitutional, or deletional variants. These variants ordinarily are prepared by site specific mutagenesis of nucleotides in the DNA encoding the p33$^{IG1}$, by which DNA encoding the variant is obtained, and thereafter expressing the DNA in recombinant cell culture. However, variant p33$^{IG1}$ fragments having up to about 100 to 150 amino acid residues are prepared conveniently by in vitro synthesis.

The amino sequence variants of the p33$^{IG1}$ are predetermined variants not found in nature or naturally occurring alleles. The p33$^{IG1}$ variants typically exhibit the same qualitative biological activity as naturally occurring p33$^{IG1}$. However, the p33$^{IG1}$ variants and derivatives that are not capable of exhibiting qualitative biological activity similar to native p33$^{IG1}$, may nonetheless be useful as reagents in diagnostic assays for p33$^{IG1}$ or antibodies to p33$^{IG1}$ Further, when insolubilized in accordance with known methods, they may be used as agents for purifying anti-p33$^{IG1}$ antibodies from antisera or hybridoma culture supernatants. Further, they may be used as immunogens for raising antibodies to p33$^{IG1}$ or as a component in an immunoassay kit (labeled so as to be a competitive reagent for native p33$^{IG1}$ or unlabeled so as to be used as a standard for the p33$^{IG1}$ assay) so long as at least one p33$^{IG1}$ epitope remains active in these analogs.

While the site for introducing an amino acid variation may be predetermined, the mutation, per se, need not be predetermined. For example, in order to optimize the performance of a mutation at a given site, random or saturation mutagenesis (where all 20 possible residues are inserted) is conducted at the target codon and the expressed p33$^{IG1}$ variant is screened for the optimal combination of desired activities. Such screening is within the ordinary skill of the art.

Amino acid insertions will usually be on the order of from about one to about ten amino acid residues; substitutions are typically introduced for single residues and deletions will range from about one to about thirty residues. Deletions or insertions preferably are made in adjacent pairs. That is, a deletion of two residues or insertion of two residues. Substitutions, deletions, insertions or any combination thereof may be introduced or combined to arrive at a final construct.

Insertional amino acid sequence variants of the native p33$^{IG1}$ are those in which one or more amino acid residues extraneous to native p33$^{IG1}$ are introduced into a predetermined site in the target p33$^{IG1}$ and which displace the pre-existing residues. Commonly, insertional variants are fusions of heterologous proteins or polypeptides to the amino or carboxyl terminus of the p33$^{IG1}$. Such variants are referred to as fusions of the p33$^{IG1}$ and a polypeptide containing a sequence which is other than that which is normally found in the p33$^{IG1}$ at the inserted position. Several groups of fusions are contemplated for carrying out the invention described herein.

Immunologically active p33$^{IG1}$ derivatives and fusions comprise the p33$^{IG1}$ and a polypeptide containing a non-p33$^{IG1}$ epitope. Such immunologically active derivatives and fusions of p33$^{IG1}$ are within the scope of this invention. The non-p33$^{IG1}$ epitope may be any immunologically competent polypeptide, i.e., any polypeptide which is capable of eliciting an immune response in the animal in which the fusion is to be administered, or which is capable of being bound by an antibody raised against the non-p33$^{IG1}$ polypeptide.

Substitutional variants are those in which at least one residue in the FIG. 2 sequence has been removed and a different residue inserted in its place. Novel amino acid sequences as well as isosteric analogs (amino acid or otherwise) are included within the scope of this invention.

Some deletions, insertions and substitutions will not produce radical changes in the characteristics in the p33$^{IG1}$ molecule. However, when it is difficult to predict the exact effect of the substitution, deletion or insertion in advance of doing so, for example, when modifying an immune epitope on the p33$^{IG1}$ protein, one skilled in the art will appreciate that the effect will be evaluated by routine screening assays. For example, a change in the immunological character of the p33$^{IG1}$ protein, such as affinity for a given antibody, is measured by a competitive-type immunoassay. Modifications of protein properties such as redox or thermal stability, hydrophobicity, susceptibility to proteotlytic degradation, or the tendency to aggregate with carriers or into multimers may be assayed by methods well known to one of skill in the art.

Deletions of cysteine or other labile amino acid residues may also be desirable. For example, they may increase the oxidative stability of the p33$^{IG1}$ protein. Deletion or substitution of potential proteolysis sites, e.g., Arg Arg, is accomplished by deleting one of the basic residues or substituting one with glutaminyl or histidyl residues.

Covalent modifications of the p33$^{IG1}$ protein are included within the scope of the present invention. Such modifications are introduced by reacting targeted amino acid residues with an organic derivatizing agent that is capable of reacting with selected side chains or terminal amino acid residues. The resulting covalent derivatives of p33$^{IG1}$ are useful to identify residues important for p33$^{IG1}$'s biological activity, for immunoassays of the p33$^{IG1}$ or for preparation of anti-p33$^{IG1}$ antibodies for immunofinity purification of recombinant p33$^{IG1}$. Such modification are within the ordinary skill of the art and are performed without undue experimentation.

In general, prokaryotes are used for cloning of DNA sequences and in constructing the vectors useful in the present invention. For example, E. coli HB101, DH5α and XL1-blue are particularly useful. These examples are meant to be illustrative and do not limit the present invention. Alternatively, in vitro methods of cloning such as the polymerase chain reaction may be used.

Expression hosts typically are transformed with DNA encoding the p33$^{IG1}$ which has been ligated into an expression vector. Such vectors ordinarily carry a replication site, although this is not necessary where chromosomal integration will occur. Expression vectors may also include marker sequences which are capable of providing phenotypic selection in transformed cells. Expression vectors also optimally will contain sequences which are useful for the control of transcription and translation.

Expression vectors used in eukaryotic host cells will also contain sequences necessary for the termination of transcription which may affect MRNA expression. Expression vectors may contain a selection gene as a selectable marker. Examples of suitable selectable markers for mammalian cells are dihydrofolate reductase, thymidine kinase, neomycin or hygromycin.

C. Pharmaceutical Compositions

The present invention may be used to block the growth of cancer cells by increasing expression of p33$^{IG1}$. Blocking the growth of cancer cells is of obvious importance and is limited mainly by our ability to deliver p33$^{IG1}$ expression constructs to target tissues. An appropriately driven antisense construct will allow blocking of p33$^{IG1}$ expression in mammalian cells. Viral vectors may be used to deliver sense and antisense constructs to target cells in vivo. Such methods are known in the art [19].

The methods of this invention may also be achieved by using a pharmaceutical composition comprising one or more of the following cancer cell proliferation inhibiting compounds: p33$^{IG1}$, its analogs and related proteins and peptides. Doses are selected to provide effective inhibition of cancer cell growth and/or proliferation. Parenteral administration is preferred, with subdermal or intramuscular administration most preferred. Intravenous administration or use of implanted milliosmol pumps (available from Alza) may also be used.

When used for parenteral administration, which is preferred, the proteins and peptides of the present invention may be formulated in a variety of ways. Aqueous solutions of the proteins or peptides of the present invention may be encapsulated in polymeric beads, liposomes, nanoparticles or other injectable depot formulations known to those of skill in the art. (Examples thereof may be found, for example, in Remington's Pharmaceutical Sciences, 18th Edition, 1990.)

Compositions including a liquid pharmaceutically inert carrier such as water may also be considered for both parenteral and oral administration. Other pharmaceutically compatible liquids may also be used. The use of such liquids is well known to those of skill in the art. (Examples thereof may be found, for example, in Remington's Pharmaceutical Sciences, 18th Edition, 1990.)

The dose level and schedule of administration may vary depending on the particular p33$^{IG1}$-related compound(s) and/or compositions used, the method of administration, and such factors as the age and condition of the subject.

As discussed previously, parenteral administration is preferred, but formulations may also be considered for other means of administration such as orally, per rectum, and transdermally. The usefulness of these formulations may depend on the particular compound used and the particular subject receiving the p33$^{IG1}$-related compound.

Oral formulations of p33$^{IG1}$-related compounds may optionally and conveniently be used in compositions containing a pharmaceutically inert carrier, including conventional solid carriers, which are conveniently presented in tablet or capsule form. Formulations for rectal or transdermal use may contain a liquid carrier that may be oily, aqueous, emulsified or contain certain solvents suitable to the mode of administration. Suitable formulations are known to those of skill in the art. (Examples thereof may be found, for example, in Remington's Pharmaceutical Sciences, 18th Edition, 1990.)

D. Use of p33$^{IG1}$ and Related Proteins and Peptides for Diagnosis and Inhibition of Breast Cancer The present invention also has diagnostic use, since simple immunochemical staining of cells or sections of cells should give an accurate estimate of the portion of cells expressing p33$^{IG1}$. Such a test based on the production and use of p33$^{IG1}$ antibodies and standard secondary techniques of visualization will be useful in cancer diagnosis. Such a test of tumor suppressor gene expression might also be useful to the scientific research community.

In a diagnostic method of the present invention, cells obtained from an individual or a culture are processed in order to determine the extent to which $p33^{IG1}$ is present in cells, in a specific cell type or in a body fluid. This can be determined using known techniques and an antibody specific for $p33^{IG1}$. Comparison of results obtained from cells or a body fluid being analyzed with results obtained from an appropriate control (e.g., cells of the same type known to have normal $p33^{IG1}$ levels or the same body fluid obtained from an individual known to have normal $p33^{IG1}$ levels) is carried out. Decreased $p33^{IG1}$ levels are indicative of an increased probability of abnormal cell proliferation or oncogenesis or of the actual occurrence of abnormal proliferation or oncogenesis. Such antibodies to $p33^{IG1}$ will generally be detectably labelled (e.g., with a radioactive label, a fluorescent material, biotin or another member of a binding pair or an enzyme).

A method of inhibiting cell division, particularly cell division which would otherwise occur at an abnormally high rate, is also possible. For example, increased cell division is reduced or prevented by introducing into cells a drug or other agent which can increase, directly or indirectly, expression of $p33^{IG1}$. In one embodiment $p33^{IG1}$ protein is introduced directly. In another embodiment nucleotides coding for $p33^{IG1}$ are introduced.

Cell division is increased by preventing transcription and/or translation of $p33^{IG1}$ DNA and/or RNA. This can be carried out by introducing antisense oligonucleotides into cells, in which they hybridize to the $p33^{IG1}$-encoding nucleic acid sequences, preventing their further processing. It is also possible to inhibit expression of $p33^{IG1}$ by the addition of agents which degrade $p33^{IG1}$. Such agents include a protease or substance which enhances $p33^{IG1}$ breakdown into cells. In either case, the effect is indirect in that less $p33^{IG1}$ is available than would otherwise be the case.

Antibodies specifically reactive with $p33^{IG1}$ can be produced, using known methods [18]. For example, anti-$p33^{IG1}$ antisera can be produced by injecting an appropriate host (e.g., rabbits, mice, rats, pigs) with $p33^{IG1}$ and withdrawing blood from the host animal after sufficient time for antibodies to have been formed. Monoclonal antibodies can also be produced using known techniques [18].

A hybridization probe prepared from a segment of nucleotides of $p33^{IG1}$-encoding RNA, $p33^{IG1}$ cDNA or $p33^{IG1}$ genomic DNA may be employed as a means for determining the number of copies of $p33^{IG1}$ present in the genomic DNA of a given sample, or the level of $p33^{IG1}$ MRNA expressed in cells of such sample.

The following examples are offered to illustrate this invention and are not meant to be construed in any way as limiting the scope of this invention.

E. EXAMPLES

The methods described as follows were used to perform the studies described herein. In addition, the generally known methods set forth in laboratory manuals for molecular cloning and antibody techniques [e.g., 17,18] may advantageously be used by one of skill in the art to produce additional embodiments of the invention.

EXAMPLE 1

Strategy for Cloning and Biological Assays

Subtractive hybridization of breast cancer cell line cDNAs with cDNA from normal mammary epithelial cells, subcloning of subtracted cDNAs into the pLNCX retroviral vector and injection into nude mice was done essentially as described [3] with the modifications noted below. The cloning of full length cDNA was done using standard methods [17]. The strategy is shown in FIG. 1a.

cDNAs from breast cancer cell lines and cDNA from a normal mammary epithelial cell line were digested with the restriction enzyme Sau 3A. Fragments of tester DNA (cDNA from normal epithelial cells) were ligated to "a" adaptors. Fragments of driver DNA (cDNA from breast tumor cells) were ligated to "b" adaptors. Adaptors were prepared by annealing the synthetic oligonucleotides:

5'-gacctggctctagaatccacgaca-3' (SEQ ID NO. 3) with

5'-gatctgtcgtgaattctagagccagg-3' (SEQ ID NO. 4) (adaptor "a"); and

5'-gactcgacgttgtaacacggcagt-3' (SEQ ID NO. 5) with 5'-gatcactgccgtgttacaacgtcgag-3'(SEQ ID NO. 6) (adaptor "b").

The mixture of driver DNA and tester DNA was denatured, then hybridized at 66° C. for 18 hours. Resultant double-stranded molecules were then selectively amplified by PCR using primer "a". The "amplicons" were then subjected to three successive rounds of hybridization, selective degradation and PCR amplification using 40 μg of driver cDNA containing adaptors and 200 ng, 5 ng and 5 μg of tester amplicons in respective rounds. Subcloning into the retroviral vector, packaging into the BOSC 23 virus-packaging cell line and assays using nude mice were performed as described [3].

Panel 1 of FIG. 1b shows NMuMG cells infected with the retroviral vector pLNCX and panel 2 of FIG. 1b shows cells infected with retroviral vector containing an antisense $p33^{IG1}$ insert. The bar equals 1 mm. Panel 3 of FIG. 1b shows NIH 3T3 cells transfected with vector alone and panel 4 of FIG. 1b shows cells transfected in parallel with vector containing the antisense $p33^{IG1}$ insert. These results showed that the antisense $p33^{IG1}$ insert caused increased cell proliferation.

Analysis of $p33^{IG1}$ protein levels in samples was performed by blotting using α-$p33^{IG1}$ antibodies raised against a GST-$p33^{IG1}$ fusion protein. As shown in FIG. 1c, we tested NMuMG (lane 1) and ZR-75 (lane 2) cell lines. Preincubation of antibodies with GST-$p33^{IG1}$ fusion protein blocked recognition of $p33^{IG1}$ in a parallel blot using lysates from the same cells (lanes 3 and 4). Western blot of lysates from NMUMG cells infected with PLNCX vector (lane 5) or pLNCX vector containing antisense $p33^{IG1}$ insert (lane 6) were also performed. The intensity of the band representing $p33^{IG1}$ was reduced by approximately 10-fold in cells infected with vector containing the antisense insert as estimated by scanning densitometry.

EXAMPLE 2 cDNA and Predicted Amino Acid Sequence of $p33^{IG1}$

The predicted coding region of $p33^{IG1}$ begins at nucleotide 109 and ends at nucleotide 739, as shown in FIG. 2. The $p33^{IG1}$ clone was sequenced in full on both strands, using an Applied Biosystems automated sequencer. Regions of the $p33^{IG1}$ protein that show homology to different members of the $p16^{MTS1}$ family of cyclin-dependent kinase inhibitors and to retinoblastoma binding protein 2 were identified using the Blast program available from the National Centre for Biological Information (address: www.ncbi.nim.nih.gov).

EXAMPLE 3

Effects of p33$^{IG1}$ Overexpression

FIG. 3a shows the results when human Hs578T breast cancer cells (panels 1 and 2) and normal fibroblasts (panels 3 and 4) were transfected with the plasmids pBK (panels 1 and 3) or p33$^{IG1}$-S (panels 2 and 4). Following growth for 3 weeks in medium containing G418, plates were fixed and stained with Coomassie Brilliant Blue to identify surviving colonies. Results show that p33$^{IG1}$ expression decreases the number of colonies formed.

As shown in FIG. 3b, normal Hs68 HDFs were injected with solutions containing p33$^{IG1}$-S plus non-specific rabbit IgG (panels 1 and 2) or with p33$^{IG1}$αS plus non-specific rabbit IgG (panels 3 and 4). Injected cells were grown in the presence of BrdU for 36 hours and were fixed and stained for the presence of co-injected IgG (panels 1 and 3) or incorporated BrdU (panels 2 and 4). Arrows identify injected cells.

FIG. 3c shows the combined results of 5 separate experiments. Each group represents 110–200 injected cells. Hs68 cells were plated on glass coverslips, deprived of serum for 12 h, microinjected with the indicated mixture of plasmid DNA (0.1 gg/ml) plus nonspecific IgG (2 μg/ml), then incubated for 36 hours in complete medium containing BrdU. Fixed cells were identified by staining for injected IgG and for the incorporation of BrdU. Microinjection, fixation and staining were done as described previously [16].

EXAMPLE 4

Levels of p33$^{IG1}$ mRNA and protein in normal young and senescent fibroblasts p33$^{IG1}$ mRNA expression in young and old cells was monitored by RT-PCR with two sets of primer pairs. These were:

5'-GAAGCGGCGGATGCTGCACT-3' (SEQ ID NO. 9) and 5'-ACGCACGAGAAGTGGAACCA-3' (SEQ ID NO. 10) for p33$^{IG1}$; and 5'-CGGAGTCAACGGATTTGGTCGTAT -3' (SEQ ID NO. 11); and 5'-AGCCTTCTCCATGGTGGTGAAGAC -3' (SEQ ID NO. 12) for the GAPDH gene.

Thirty-two PCR cycles for p33$^{IG1}$ and twenty-two cycles for GAPDH were performed. Primers for GAPDH were added to PCR tubes at the ending of the 10th cycle.

Proteins were separated by electrophoresis in 12.5% polyacrylamide/SDS gels, and transferred to membranes for 1h using an electroblotter. The membranes were blocked in TES (100 mM Tris, 150 mM NaCl) containing 10% nonfat dried milk and 0.1% Tween-20, for 2 hours. Incubation of the membranes with p33$^{IG1}$ antiserum are performed in TBS containing 5% nonfat milk and 0.1% Tween-20 for 1h and then membranes were washed with TBST solution for 30 min. Horseradish peroxidase-conjugated goat anti-rabbit antibody was then applied to the filters for 1h in TEST. Peroxidase activity was detected using ECL (Amersham).

The results shown in FIG. 4a demonstrate that p33$^{IG1}$ MRNA expression was lower in young (Y) than in senescent (O) Hs68 cells (30 and 82 population doublings, respectively). In FIG. 4b, the arrows indicate the signals obtained when cell lysates containing equal amounts of protein from low-passage (Y) or high passage (O) Hs68 cells were examined by immunoblot analysis with antibody against p33$^{IG1}$ protein. The p33$^{IG1}$ protein was found in greater amounts in senescent cells.

TABLE 1

Results of the soft agar and focus forming assays.

| Trial | Soft agar assay | | | | | Focus forming assay | | |
|---|---|---|---|---|---|---|---|---|
| Number | 1 | 2 | 3 | 4 | mean | 1 | 2 | mean |
| pLNCX (vector) | 0 | 0 | 0 | 0 | 0 | 9 | 13 | 11 |
| pLNCX-Ras | 224 | 248 | 208 | (—) | 226.7 | (—) | (—) | (—) |
| pLNCX-αS | 42 | 46 | 41 | 82 | 52.8 | 18 | 34 | 26 |
| pLNCX-S | (—) | (—) | 0 | 0 | 0 | (—) | (—) | (—) |

(—) = not determined

To obtain these data, 105 virus-infected NMuMG cells per plate were seeded in soft agar in 10 cm plates and incubated at 37° C. for 6–7 weeks prior to scoring colonies. 5×10$^5$ transfected NIH 3T3 cells were plated per 10 cm dish. Transfected NIH 3T3 cells were grown in 5% serum for 4 weeks prior to fixing and visualizing foci. PLNCX-S and pLNCX-αS represent sense and antisense orientations of the p33$^{IG1}$ gene, respectively.

(–)=not determined

TABLE 2

Overexpression of p33$^{IG1}$ arrested cells in G0/G1

| | pBK (vector) | | | pBK- p33$^{IG1}$-S | | |
|---|---|---|---|---|---|---|
| | G1/G0 | S | G2/M | G1/G0 | S | G2/M |
| Trial 1 | 32.7 | 38.5 | 28.8 | 53.3 | 19.9 | 26.8 |
| Trial 2 | 34.5 | 35.9 | 29.6 | 72.8 | 19.7 | 7.5 |
| mean | 33.6 | 37.2 | 29.2 | 63.1 | 19.8 | 17.2 |

To obtain these data, Hs68 cells were cotransfected with pCMV-CD20 together with pBK-p33$^{IG1}$-S or with pBK vector as a negative control. Cells were fixed and stained for CD20 expression using commercially available antibodies and with propidium iodide 48 hours after electroporation. Cell cycle distribution was determined by flow cytometry using fluorescence-activated cell sorting. The percentage of the CD20+ cells in different phases of the cell cycle is shown for two independent experiments.

Modification of the above-described modes of carrying out various embodiments of this invention will be apparent to those skilled in the art following the teachings of this invention as set forth herein. The examples described above are not limiting, but are merely exemplary of this invention, the scope of which is defined by the following claims.

What is claimed is:

1. A method of identifying a DNA sequence which is the p33$^{IG}$ DNA sequence showvn in SEQ ID No. 1, comprising
   a) subtractively hybridizing breast cancer cell line cflNAs with cDNA from normal mammary epithelial cells to obtain subtracted fractions;
   b) combining said subtracted fractions and using them to probe a cDNA library
   c) isolating cDNA clones obtained from step b) and randomly fragmenting them;
   d) transferring said DNA fragments to an expression vector to yield a genetic suppressor element library;
   e) introducing said genetic suppressor element library into normal cells;
   f) using the infected cells from step e) in a system which provides a means to identify an antisense oriented clone;
   g) selecting said antisense oriented clone; and
   h) isolating the cDNA of SEQ ID No. 1 from the clones selected in step g).

2. The method of claim 1 which uses a positive selection procedure comprising in vivo selection.

3. A method of identifying a nucleic acid sequence which encodes the amino acid sequence of SEQ ID No 2 comprising
   a) subtractively hybridizing breast cancer cell line cDNAs with cDNA from normal mammary epithelial cells to obtain subtracted fractions;
   b) combining said subtracted fractions and using them to screen a cDNA library;
   c) isolating cDNA clones obtained from step b) and randomly fragmenting them;
   d) transferring said DNA fragments to an expression vector to yield a genetic suppressor element libary
   e) introducing said genetic suppressor element librgy into normal cells
   f) using the infected cells from step e) in a system which provides a means to identify an antisense oriented clone;
   g) selecting said antisense oriented clone; and
   h) isolating a cDNA which encodes the amino acid sequence of SEQ ID No 2 from the clones selected in step g).

4. The method of claim 3 which uses a positive selection procedure comprising in vivo selection.

5. The method of claim 1, wherein said system of step f) is an immune deficient animal, which method further comprises the steps of.
   a) identifying and selecting animals which form tumors and isolating putative transforming fragments from said tumors;
   b) transferring said putative transforming fragments to an expression vector and introducing said expression vector containing said putative transforming fragments into normal cells;
   c) identifying and selecting those cells from step b) showving increased cell proliferation; and
   d) isolating the cDNA of SEQ ID No 1 from the cells selected in step c).

6. The method of claim 3, wherein said system of step f) is an immune deficient animal, which method further comprises the steps of:
   a) identifying and selecting animals which form tumors and isolating putative transforming fragments from said tumors;
   b) transferring said putative transforming fragments to an expression vector and introducing said expression vector containing said putative transforming fragments into normal cells;
   c) identifying and selecting those cells from step b) showing increased cell proliferation; and
   d) isolating a cDNA which encodes the amino acid sequence of SEQ ID No 2 from the cells selected in step c).

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
       (A) LENGTH: 1902 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: CDS
       (B) LOCATION: 109..738

(xi) SEQUENCE DESCRIPTION: SEQ ID NO:1:

```
CTGACCCGAG GGTGGGGCCG CGCGTGGCCG TGGAAACAGA TCCTGAAGGA GCTAGACGAG        60

TGCTACGAGC GCTTCAGTCG CGAGACAGAC GGGGCGCAGA AGCGGCGG ATG CTG CAC       117
                                                     Met Leu His
                                                       1

TGT GTG CAG CGC GCG CTG ATC CGC AGC CAG GAG CTG GGC GAC GAG AAG       165
Cys Val Gln Arg Ala Leu Ile Arg Ser Gln Glu Leu Gly Asp Glu Lys
      5                  10                  15

ATC CAG ATC GTG AGC CAG ATG GTG GAG CTG GTG GAG AAC CGC ACG CGG       213
Ile Gln Ile Val Ser Gln Met Val Glu Leu Val Glu Asn Arg Thr Arg
 20                  25                  30                  35

CAG GTG GAC AGC CAC GTG GAG CTG TTC GAG GCG CAG CAG GAG CTG GGC       261
Gln Val Asp Ser His Val Glu Leu Phe Glu Ala Gln Gln Glu Leu Gly
                 40                  45                  50

GAC ACA GTG GGC AAC AGC GGC AAG GTT GGC GCG GAC AGG CCC AAT GGC       309
Asp Thr Val Gly Asn Ser Gly Lys Val Gly Ala Asp Arg Pro Asn Gly
             55                  60                  65

GAT GCG GTA GCG CAG TCT GAC AAG CCC AAC AGC AAG CGC TCA CGG CGG       357
Asp Ala Val Ala Gln Ser Asp Lys Pro Asn Ser Lys Arg Ser Arg Arg
         70                  75                  80

CAG CGC AAC AAC GAG AAC CGT GAG AAC GCG TCC AGC AAC CAC GAC CAC       405
Gln Arg Asn Asn Glu Asn Arg Glu Asn Ala Ser Ser Asn His Asp His
     85                  90                  95

GAC GAC GGC GCC TCG GGC ACA CCC AAG GAG AAG AAG GCC AAG ACC TCC       453
Asp Asp Gly Ala Ser Gly Thr Pro Lys Glu Lys Lys Ala Lys Thr Ser
100                 105                 110                 115

AAG AAG AAG AAG CGC TCC AAG GCC AAG GCG GAG CGA GAG GCG TCC CCT       501
Lys Lys Lys Lys Arg Ser Lys Ala Lys Ala Glu Arg Glu Ala Ser Pro
                120                 125                 130

GCC GAC CTC CCC ATC GAC CCC AAC GAA CCC ACG TAC TGT CTG TGC AAC       549
Ala Asp Leu Pro Ile Asp Pro Asn Glu Pro Thr Tyr Cys Leu Cys Asn
            135                 140                 145

CAG GTC TCC TAT GGG GAG ATG ATC GGC TGC GAC AAC GAC GAG TGC CCC       597
Gln Val Ser Tyr Gly Glu Met Ile Gly Cys Asp Asn Asp Glu Cys Pro
        150                 155                 160

ATC GAG TGG TTC CAC TTC TCG TGC GTG GGG CTC AAT CAT AAA CCC AAG       645
Ile Glu Trp Phe His Phe Ser Cys Val Gly Leu Asn His Lys Pro Lys
    165                 170                 175

GGC AAG TGG TAC TGT CCC AAG TGC CGG GGG GAG AAC GAG AAG ACC ATG       693
Gly Lys Trp Tyr Cys Pro Lys Cys Arg Gly Glu Asn Glu Lys Thr Met
180                 185                 190                 195

GAC AAA GCC CTG GAG AAA TCC AAA AAA GAG AGG GCT TAC AAC AGG           738
```

-continued

```
Asp Lys Ala Leu Glu Lys Ser Lys Lys Glu Arg Ala Tyr Asn Arg
            200                 205                 210

TAGTTTGTGG ACAGGCGCCT GGTGTGAGGA GGACAAAATA AACCGTGTAT TTATTACATT      798

GCTGCCTTTG TTGAGGTGCA AGGAGTGTAA AATGTATATT TTTAAAGAAT GTTAGAAAAG      858

GAACCATTCC TTTCATAGGG ATGGCAGTGA TTCTGTTTGC CTTTTGTTTT CATTGGTACA      918

CGTGTAACAA GAAAGTGGTC TGTGGATCAG CATTTTAGAA ACTACAAATA TAGGTTTGAT      978

TCAACACTTA AGTCTCAGAC TGATTTCTTG CGGGAGGAGG GGGACTAAAC TCACCCTAAC     1038

ACATTAAATG TGGAAGGAAA ATATTTCATT AGCTTTTTTA TTTTAATACA AGTAATATTA     1098

TTACTTTATG AACAATTTTT TTTAATTGGC CATGTCGCCA AAAATACAGC CTATAGTAAA     1158

TGTGTTTCTT GCTGCCATGA TGTATATCCA TATAACAATT CAGTAACAAA GGTTTAAAGT     1218

TTGAAGATTA TTTTTTAAAA AGGTAAAAGG TTAAATTTTA CATGACAGAT ATTTTATCTA     1278

TTGGCCTGTT CCCCAAATGG CCATTTTAAA ATGCTTGGGT ACACTTCTCT TAAGTGGTCT     1338

AGTCAAGGAA CCTCAAGTCA TGCTTTTGCT ATCACCAATC ATAGTGTACC CATCTTTAAT     1398

TTATATCAGG TGTATAAATG TACATTTCCA AATGAACTTG CACTGTAATA TTATAATTGG     1458

AAGTGCAGTC AGCAGTAGCT GTCGGAGCTA ATGTCACAAT TATGTGCAAA GGTGTGCTTC     1518

CTGCTGTATG TGAGCTGTAA AAATGTTACG TGAAGAAATA AATGAAACTT GGCCAGTTTG     1578

TTCCTCTAGT AGTATATTTA ATTTTGACAT AAGTAACTTT TAAAATTTGT CTTAAAAATT     1638

TATACACCAG CAATTTAGAC AAAGCCTTAA GCAAATTTTG TATTATTGTT CTCACTTATT     1698

ATTAATAATG AAGTAGAAGT TACTTAATTG CCAGCAAATA AATACGTGTC AAAAAAGAAT     1758

CTGTATTCAG ACCCCTGGGG TCAGGAAATT ACTGCCCCAC TTGTCAAGTT CAGCCCACCA     1818

TCTGTTTGAA CATTATATGA AGTTTAAATT CTAGTGTCCA TAAATAAAGT TTCAGCGGCA     1878

CCCCAAAAAA AAAAAAAAAA AAAA                                           1902

(2) INFORMATION FOR SEQ ID NO:2:

(i) SEQUENCE CHARACTERISTICS:
         (A) LENGTH: 210 amino acids
         (B) TYPE: amino acid
         (D) TOPOLOGY: linear (ii) MOLECULE TYPE: protein (xi) SEQUENCE DESCRIPTION: SEQ ID NO:2:

Met Leu His Cys Val Gln Arg Ala Leu Ile Arg Ser Gln Glu Leu Gly
  1               5                  10                  15

Asp Glu Lys Ile Gln Ile Val Ser Gln Met Val Glu Leu Val Glu Asn
             20                  25                  30

Arg Thr Arg Gln Val Asp Ser His Val Glu Leu Phe Glu Ala Gln Gln
         35                  40                  45

Glu Leu Gly Asp Thr Val Gly Asn Ser Gly Lys Val Gly Ala Asp Arg
     50                  55                  60

Pro Asn Gly Asp Ala Val Ala Gln Ser Asp Lys Pro Asn Ser Lys Arg
 65                  70                  75                  80

Ser Arg Arg Gln Arg Asn Asn Glu Asn Arg Glu Asn Ala Ser Ser Asn
                 85                  90                  95

His Asp His Asp Asp Gly Ala Ser Gly Thr Pro Lys Glu Lys Lys Ala
            100                 105                 110

Lys Thr Ser Lys Lys Lys Arg Ser Lys Ala Lys Ala Glu Arg Glu
        115                 120                 125
```

```
Ala Ser Pro Ala Asp Leu Pro Ile Asp Pro Asn Glu Pro Thr Tyr Cys
        130                 135                 140
Leu Cys Asn Gln Val Ser Tyr Gly Glu Met Ile Gly Cys Asp Asn Asp
145                 150                 155                 160
Glu Cys Pro Ile Glu Trp Phe His Phe Ser Cys Val Gly Leu Asn His
                165                 170                 175
Lys Pro Lys Gly Lys Trp Tyr Cys Pro Lys Cys Arg Gly Glu Asn Glu
            180                 185                 190
Lys Thr Met Asp Lys Ala Leu Glu Lys Ser Lys Lys Glu Arg Ala Tyr
        195                 200                 205
Asn Arg
210
```

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
GACCTGGCTC TAGAATCCAC GACA                                        24
```

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
GATCTGTCGT GAATTCTAGA GCCAGG                                      26
```

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
GACTCGACGT TGTAACACGG CAGT                                        24
```

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
GATCACTGCC GTGTTACAAC GTCGAG                                      26
```

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CCCCAAGCTT GTTAACTTCG ATGGA                                      25

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ATGGCGTTAC TTAAGCTAGC TTGC                                       24

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GAAGCGGCGG ATGCTGCACT                                            20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

ACGCACGAGA AGTGGAACCA                                            20

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CGGAGTCAAC GGATTTGGTC GTAT                                       24

(2) INFORMATION FOR SEQ ID NO:12:

(i) SEQUENCE CHARACTERISTICS:
        (A) LENGTH: 24 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

AGCCTTCTCC ATGGTGGTGA AGAC                                              24
```